United States Patent [19]

Loffelman

[11] 4,386,177

[45] May 31, 1983

[54] LIGHT STABILIZERS FOR POLYMERS CONTAINING HINDERED PIPERIDINYL-SUBSTITUTED 1,3,5 TRIAZINE GROUPS

[75] Inventor: Frank F. Loffelman, Bridgewater, N.J.

[73] Assignee: American Cyanamid Company, Stamford, Conn.

[21] Appl. No.: 284,884

[22] Filed: Jul. 20, 1981

[51] Int. Cl.$^3$ .................. C07D 401/14; C07D 413/14; C08K 5/34; C08K 5/35

[52] U.S. Cl. ................................... 524/100; 524/97; 544/113; 544/198

[58] Field of Search ................ 528/423, 424; 544/113, 544/198, 209, 204, 206, 207; 260/45.8 NP, 45.8 NT

[56] References Cited

U.S. PATENT DOCUMENTS

| | | | |
|---|---|---|---|
| 3,697,520 | 10/1972 | Winter | 544/196 |
| 4,006,274 | 1/1977 | Chance et al. | 544/196 |
| 4,086,204 | 4/1978 | Cassandrini et al. | 260/45.8 NT |
| 4,104,248 | 8/1978 | Cantatore | 260/45.8 NP |
| 4,294,963 | 10/1981 | Rody | 544/209 |
| 4,297,492 | 10/1981 | Rasberger et al. | 544/197 |
| 4,315,859 | 2/1982 | Nikles | 544/198 |
| 4,348,493 | 9/1982 | Loffelman | 524/100 |

OTHER PUBLICATIONS

The Condensed Chemical Dictionary, 8th Edition, edited by Gessner G. Hawley, p. 644, regarding definition of "oligomer", Van Nostrand Reinhold Company (1971).

Hack's Chemical Dictionary, 4th Edition, edited by Julius Grant, p. 473, regarding definition of "oligomer", McGraw Hill Book Company (1969).

*Primary Examiner*—V. P. Hoke
*Attorney, Agent, or Firm*—Steven J. Hultquist

[57] ABSTRACT

Oligomers prepared from alkoxycarbonylalkyleneamino halotriazines and diamines are useful as light stabilizers for polymers subject to ultraviolet radiation degradation.

13 Claims, No Drawings

LIGHT STABILIZERS FOR POLYMERS CONTAINING HINDERED PIPERIDINYL-SUBSTITUTED 1,3,5 TRIAZINE GROUPS

This invention relates to certain novel oligomers and to their use as light stabilizers for polymers. More particularly, this invention relates to novel oligomers of the formula (I)

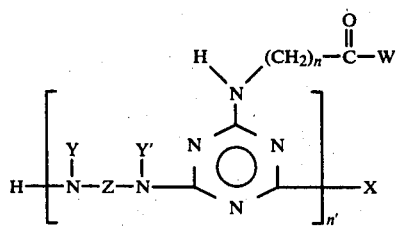

wherein W represents $C_1$–$C_{20}$ alkoxy, or

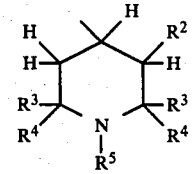

wherein $R^2$ represents hydrogen, $C_1$–$C_{18}$ alkyl, or benzyl; $R^3$ and $R^4$ independently represent $C_1$–$C_8$ alkyl, benzyl, or phenethyl, or together with the carbon to which they are attached form a $C_5$–$C_{10}$ cycloalkyl; $R^5$ represents hydrogen, $C_2$–$C_3$ hydroxyalkyl, $C_1$–$C_8$ alkyl, hydroxyl, or oxyl; Z represents $C_2$–$C_{20}$ alkylene, either straight-chained or branched, wherein the alkylene chain may be interrupted by oxy, thio, or

radicals, wherein $R^6$ represents hydrogen, $C_1$–$C_{20}$ alkyl, or the radical (II); $C_5$–$C_{10}$ cycloalkylene,

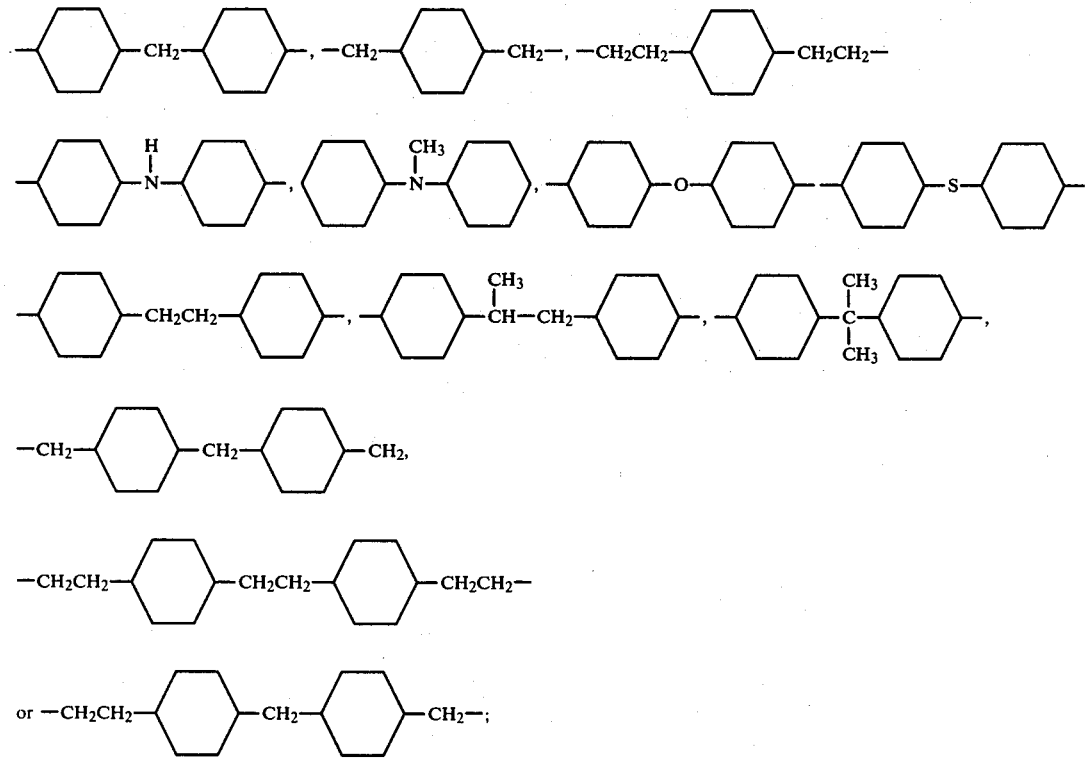

wherein R and $R^1$, which are the same or different, represent hydrogen or $C_1$–$C_{18}$ alkyl; n is an integer from 1 to 3; Y and $Y^1$, which are the same or different, represent hydrogen, $C_1$–$C_{20}$ alkyl, or the radical (II)

$C_6$–$C_{12}$ arylene, or $C_8$–$C_{14}$ aralkylene, n' is an integer greater than 1, and X represents halo, $C_1$–$C_8$ alkylamino, di($C_1$–$C_8$)alkylamino, pyrrolidyl, or morpholino, with the proviso that at least one moiety of formula (II) is present in the repeating unit.

The preferred oligomers of formula (I) are those wherein Y and Y' are the moiety (II).

The especially preferred oligomers are those wherein Y and Y' are each 2,2,6,6-tetramethyl-4-piperidinyl, and Z is hexamethylene.

The invention also relates to the use of such oligomers for stabilizing polymers, particularly polyolefins, against degradation by ultraviolet radiation, and to the stabilized compositions obtained thereby.

It is well-known that sunlight and other sources of ultraviolet radiation cause degradation of polymers as evidenced by embrittlement or yellowing of plastic articles made therefrom. It is also well-known that this degradation can be inhibited by use of ultra-violet light stabilizers incorporated in or on such articles.

Cassandrini and Tozzi, U.S. Pat. No. 4,086,204, disclose the stabilization of polymers against degradation by light by the use of polytriazine compounds prepared by reacting a 2,4-dichloro-6-alkylamino-1,3,5-triazine, such as 2,4-dichloro-6-t-octylamino-1,3,5-triazine, and a bifunctional compound containing a tetra-alkylpiperidine radical, such as 1,6-bis(2,2,6,6-tetramethyl-4-piperidylamino)hexane. Since these polytriazines have been found to be not completely satisfactory, research continues in order to find compounds, or combinations of compounds, which will be more satisfactory. The present invention arose out of such research and resulted in the discovery of the novel polytriazines of formula (I) which provide improved light stability for polymers in mono and multifilaments.

The stabilizers of the present invention offer the following advantages:

(1) excellent light-stabilizing activity,
(2) excellent compatibility with resins,
(3) high resistance to gas fading,
(4) low extractability from polymers by laundering or dry cleaning, and
(5) excellent oven-aging stability.

The oligomers of formula (I) may be prepared by reacting essentially equal molecular proportions of a compound of formula (III)

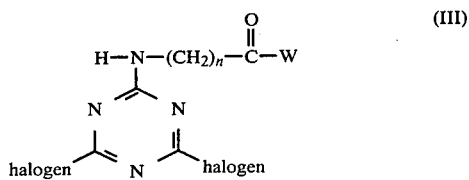

wherein W and n, are as previously defined, and a diamine of formula (IV)

wherein Y, Y' and Z are as previously defined in an inert solvent in the presence of an organic or inorganic base, at an elevated temperature, preferably at the boiling point of the solvent.

Upon completion of the reaction, the reaction mixture may be filtered to separate by-product salts and the solvent may be evaporated from the filtrate to obtain a gummy residue which may be subsequently extracted in boiling petroleum ether, filtered, and recovered from the filtrate upon evaporation of the petroleum ether.

The diamine of formula (IV) may be generally prepared by reductively alkylating a 4-oxopiperidine of formula (V) with an appropriate diamine of formula (VI) and hydrogen in the presence of a precious metal catalyst, such as platinum, as shown below.

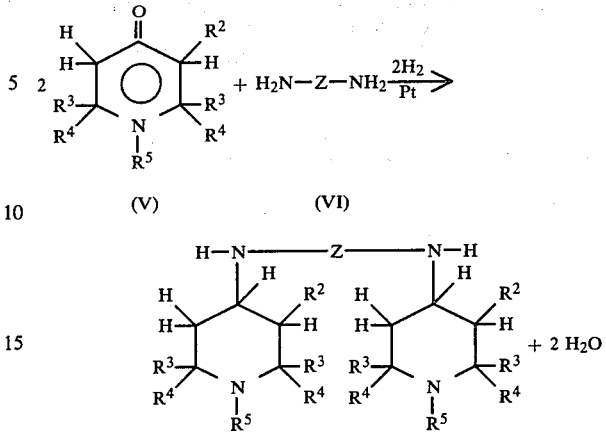

Suitable inert solvents include toluene, xylene, dioxane, and the like.

Suitable bases include sodium hydroxide, sodium carbonate, sodium bicarbonate, potassium hydroxide, potassium carbonate, potassium bicarbonate, triethylamine, tributylamine, and the like.

The compounds of formula (III) may be prepared by reacting one molecular proportion of a suitable alkoxycarbonylalkyleneamine hydrochloride, with one molecular proportion of a cyanuric halide, preferably cyanuric chloride, in an inert solvent in the presence of an organic, or inorganic base, filtering off by-product salt, and recovering the product from the filtrate.

Illustrative examples of suitable compounds of formula (III) include the following:

2,4-dichloro-6-ethoxycarbonylmethyleneamino-1,3,5-triazine,
2,4-dichloro-6-n-butoxycarbonylmethyleneamino-1,3,5-triazine,
2,4-dibromo-6-methoxycarbonylmethyleneamino-1,3,5-triazine,
2,4-dibromo-6-n-hexyloxycarbonylmethyleneamino-1,3,5-triazine,
2,4-dichloro-6-(2-ethylhexyl)oxycarbonylmethyleneamino-1,3,5-triazine,
2,4-dichloro-6-ethoxycarbonylethyleneamino-1,3,5-triazine,
2,4-dichloro-6-octadecyloxycarbonylethyleneamino-1,3,5-triazine,
2,4-dichloro-6-n-butoxycarbonyltrimethyleneamino-1,3,5-triazine,
2,4-dichloro-6-ethoxycarbonyltrimethyleneamino-1,3,5-triazine,
2,4-dichloro-6-aminocarbonylmethyleneamino-1,3,5-triazine,
2,4-dichloro-6-dimethylaminocarbonylethyleneamino-1,3,5-triazine,
2,4-dichloro-6-dodecylaminocarbonyltrimethyleneamino-1,3,5-triazine,
2,4-dichloro-6-octadecylaminocarbonylmethyleneamino-1,3,5-triazine,
and the like.

The preferred compound of Formula (III) is 2,4-dichloro-6-ethoxycarbonylmethyleneamino-1,3,5-triazine.

Illustrative examples of suitable diamines of Formula (IV) include the following:

4,4'-(dimethylenediimino)bis (2,2,6,6-tetramethylpiperidine),
4,4'-(tetramethylenediimino)bis (2,6-di-n-butyl-2,6-dimethylpiperidine),
4,4'-(hexamethylenediimino)bis (2,2,6,6-tetramethylpiperidine),
4,4'-(thiodiethylenediimino)bis (2,2,6,6-tetraethylpiperidine),
4,4'-(oxydihexamethylenediimino)bis (2,2,6,6-tetramethylpiperidine),
4,4'-(hexamethylenediimino)bis (1,2,2,6,6-pentamethylpiperidine),
4,4'-(hexamethylenediimino)bis (1-oxyl-2,2,6,6-tetramethylpiperidine),
4,4'-(hexamethylenediimino)bis(1-hydroxy-2,2,6,6-tetramethylpiperidine),
4,4'-(octadecamethylenediimino)bis(2,2,6,6-tetramethylpiperidine),
4,4'-(iminodiethylenediimino)bis(2,2,6,6-tetramethylpiperidine),
4,4'-(1,4-cyclohexylenediimino)bis(2,2,6,6-tetramethylpiperidine),
4,4'-(methylenedi-4,1-cyclohexylenediimino)bis(2,2,6,6-tetramethylpiperidine),
4,4'-[1,4-cyclohexylenebis(methyleneimino)]bis(2-benzyl-2,6,6-trimethylpiperidine),
15,15'-(hexamethylenediimino)bis(7-azadispiro[5.1.5.3-]hexadecane),
4,4'-(1,4-phenylenediimino)bis(2,2,6,6-tetramethylpiperidine),
4,4'-[1,4-phenylenedi(methyleneimino)]bis(2,2,6,6-tetramethylpiperidine),
4,4'-(hexamethylenediimino)bis(2-phenethyl-2,6,6-trimethylpiperidine),
4,4'-(hexamethylenediimino)bis(2,2,3,6,6-pentamethylpiperidine),
4-[(6-aminohexyl)amino]-2,2,6,6-tetramethylpiperidine,
4-[(12-aminododecyl)amino]-2,2,6,6-tetramethylpiperidine,
4-[bis(2-aminoethyl)amino]-2,2,6,6-tetramethylpiperidine,
4-[(4-aminocyclohexyl)amino]-2,2,3,6,6-pentamethylpiperidine,
and the like.

The preferred diamine of formula (IV) is 4,4'-(hexamethylenediimino)bis(2,2,6,6-tetramethylpiperidine), also known as 1,6-bis(2,2,6,6-tetramethyl-4-piperidylamino)hexane, and as N,N'bis(2,2,6,6-tetramethyl-4-piperidyl)hexamethylenediamine, the preparation of which is described in Example 2 of U.S. Pat. No. 4,104,248.

Preferably, the gummy residue is further reacted with an amine to minimize the halogen content of the residue. Suitable amines which may be used for this purpose include n-butylamine, n-hexylamine, n-octylamine, tert.-butylamine, morpholine, pyrrolidine, and the like.

The oligomers of this invention are useful as light stabilizers for thermoplastic substrates such as polyolefins, polyesters, polyethers, polyurethanes, polystyrenes, high-impact polystyrenes, and the like. Preferably, the thermoplastic substrate is a polyolefin.

As used herein, the term "polyolefin" includes homopolymers of alpha olefins such as polyethylene, polypropylene, polybutadiene, polyisoprene, polystyrene, and the like; copolymers of alpha olefins such as ethylene-propylene copolymer, ethylene-butylene copolymer, ethylenevinyl acetate copolymer, styrene-butadiene copolymer, acrylonitrile-butadiene-styrene terpolymer, and the like. The preferred polyolefin is a polypropylene.

Other organic materials susceptible to degradation by the effects of light, the properties of which are improved by the incorporation therein of an oligomer of this invention, include natural and synthetic rubbers; the latter include, for example, homo-, co- and terpolymers of acrylonitrile, butadiene and styrene, and blends thereof.

The oligomers of the present invention are particularly useful as light stabilizers for mono and multi-filament fibers, more particularly polypropylene mono and multifilament fibers.

Generally, the compositions comprise a polymer substrate containing from about 0.1% to about 5% by weight of the oligomer of formula (I), based on the weight of the polymer substrate.

Preferably, the composition comprises a polyolefin containing from about 0.2% to about 2% by weight of the oligomer of formula (I), based on the weight of the polyolefin.

Optionally, the compositions may contain other additives, especially additives useful in polyolefins, such as antioxidants, supplemental light stabilizers, plasticizers, flame retardants, antistatic and antislipping agents, fillers, dyes, pigments, and the like.

Suitable antioxidants include those of the hindered phenol type, such as 2,6-di-t-butyl-p-cresol; 4,4'-methylenebis(2,6-di-t-butylphenol); 4,4'-methylenebis(2,6-diisopropylphenol); 2,4,6-tri-t-butylphenol; 2,2'thiobis(4-methyl-6-t-butylphenol); octadecyl 2-(3',5'-di-t-butyl-4'-hydroxyphenyl)propionate; 1,3,5-tris(4-tert-butyl-3-hydroxy-2,6-dimethylbenzyl)-1,3,5-triazine-2,4,6(1H,3H,5H)-trione; esters of thiodipropionic acid, such as dilauryl thiodipropionate and distearyl thiodipropionate, etc; hydrocarbyl phosphites, such as triphenyl phosphite, trinonyl phosphite, diisodecyl pentaerythrityl diphosphite, diphenyldecyl phosphite, etc; and combinations thereof.

Suitable supplemental light stabilizers include those of the benzotriazole class, such as 2-(2'-hydroxy-5-t-octylphenyl)benzotriazole; 2-(2'-hydroxy-3'-5'-di-t-butylphenyl)-5-chlorobenzotriazole; those of the hydroxybenzophenone type, such as 2-hydroxy-4-methoxybenzophenone; 2-hydroxy-4-octyloxybenzophenone; 2,2'-dihydroxy-4,4'-di-methoxybenzophenone; hindered phenol esters, such as n-hexadecyl 3,5-di-t-butyl-4-hydroxybenzoate, and 2',4'-di-t-butylphenyl 3,5-di-t-butyl-4-hydroxybenzoate; metal complexes, such as nickel complexes of 2,2'-thiobis(4-t-octylphenol); nickel butylamine complex of 2,2'-thiobis(4-t-octylphenol); nickel complexes of bis(4-t-octylphenyl)sulfone; nickel dibutyl dithiocarbamate; nickel salts of 4-hydroxy-3,5-di-t-butylbenzyl phosphonic acid monoalkyl esters where alkyl is methyl, ethyl, propyl, butyl, etc; nickel complex of 2-hydroxy-4-methylphenyl undecyl ketone oxime, etc. Further illustrative examples of suitable antioxidants and supplemental light stabilizers can be found in columns 3 and 4 of U.S. Pat. Nos. 3,488,290 and 3,496,134, and in the other patents mentioned therein.

As with the oligomer of formula (I), the additive is advantageously employed within the range from about 0.2% to about 2% by weight, based on the weight of the untreated polymer.

The oligomer of formula (I) may be incorporated into the polymeric substrate by any of the known techniques for compounding additives with a polymer. For example, the oligomer of formula (I) and the additive may be compounded by dry blending with the substrate in powder or granular form, followed by milling, Banbury mixing, molding, casting, extruding, swelling, and the like. Alternatively, the oligomer of formula (I) may be added, as a solution or slurry in a suitable inert solvent, or dispersant, to the polymeric substrate in powder or granular form, the whole mixed intimately in a mixer, and the solvent subsequently removed. As a further possibility, the oligomer of formula (I) may be added to the polymeric substrate during the preparation of the latter, for instance at the latex stage of polymer production, to provide prestabilized polymer material.

To incorporate the oligomer of formula (I) in multifilament fibers, the oligomer may be dry blended with the polymeric substrate and a processing antioxidant, and the blend extruded and pelletized at an elevated temperature. The pellets may then be re-extruded as multifilaments and spun into a yarn which is then drawn at an elevated temperature.

Optionally, the spun yarn may be treated with a processing lubricant. Preferably, it is treated with an ethoxylated fatty acid, or an alkoxylated glycol.

The ethoxylated fatty acid lubricants have the general formula (VII):

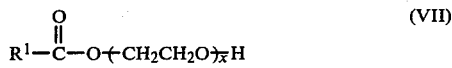
(VII)

wherein $R^1$ is an alkyl group containing from about 12 to 20 carbon atoms and x is an integer of about 2 to 20. Such compounds include the polyethoxylated fatty acids, capric acid, lauric acid, myristic acid, palmitic acid, hexadecanoic acid, stearic acid, eicosanoic acid, and the like. The preferred ethoxylated fatty acid is stearic acid ethoxylated with about 6–10 moles of ethylene oxide.

The alkoxylated glycol lubricants are of the type shown in formula (VIII):

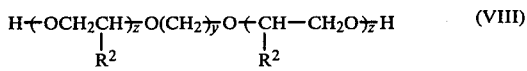
(VIII)

wherein y is an integer of 2 to 4; $R^2$ is hydrogen or methyl; and z is an integer sufficient to provide a molecular weight of about 250 to 1000. The glycols may be alkoxylated using ethylene oxide, propylene oxide, or mixtures thereof. Glycols include ethylene glycol, propylene glycol, and butylene glycol.

More preferably, the polymer mixture is spun, using as the lubricant an aqueous solution (about 15%) of (1) polyoxyethylene (6–10 moles) stearate or (2) alkoxylated (50/50 ethylene/propylene oxide) ethylene glycol (mol wt about 250). The spun, drawn yarns are then exposed to a xenon arc lamp.

In the following non-limiting examples all parts and percents are by weight unless otherwise specified.

EXAMPLE 1

2,4-Dichloro-6-ethoxycarbonylmethyleneamino-1,3,5-triazine (2.5 grams; 0.01 mole), 4,4'-(hexamethylenediimino)bis(2,2,6,6-tetramethylpiperidine) (3.9 grams; 0.01 mole), and powdered sodium hydroxide (0.8 gram; 0.02 mole) are refluxed in toluene (150 mls) for 18 hours. After removing by-product sodium chloride by filtration, the filtrate is heated under vacuum to evaporate the solvent. The gummy residue is treated with petroleum ether, heated to boiling, and filtered. Evaporation of the filtrate gives a gum which is dried in a vacuum oven at 60° C.

EXAMPLE 2

The procedure of Example 1 is followed except that 0.08 mole of 2,4-dichloro-6-ethoxycarbonylmethyleneamino-1,3,5-triazine, 0.08 mole of 4,4'-(hexamethylenediimino)bis(2,2,6,6-tetramethylpiperidine), and 0.16 mole of powdered sodium hydroxide are refluxed in toluene (600 mls) for 19 hours. n-Butylamine (1.5 grams; 0.015 mole) is then added to the reaction mixture and heating at reflux is continued for 3 more hours. After removing insolubles by filtration, the filtrate is heated under vacuum to evaporate the solvent. The resulting white gum is slurried in boiling toluene (600 mls), and filtered to separate insoluble material. The filtrate is then heated under vacuum to evaporate the solvent and obtain a gum which weighs 11.0 grams after drying over anhydrous calcium chloride at ambient temperature. The number average molecular weight of this product is 1034.

EXAMPLE 3

Unstabilized polypropylene (Pro-fax ® 6401; Hercules, Inc., Wilmington, Del.) is dry blended with 0.25% of the product of Example 2, 0.05% of calcium stearate, and 0.1% of an antioxidant (Good-rite ® 3114; B. F. Goodrich Company, Cleveland, Ohio) based on the weight of the polypropylene, and compounded in an extruder under the following conditions:

| | |
|---|---|
| rear zone | 204° F. |
| zone 1 | 216° F. |
| zone 2 | 227° F. |
| nozzle | 227° F. |
| machine speed 80–90 revolutions per minute | |

The resulting strand is pelletized and the pellets are spun through a 30-hole (0.020" d.×0.040") spinnerette under the following conditions:

| | | |
|---|---|---|
| Temperature - | spin pack | 510° F. |
| | pump block | 505° F. |
| | smear head | 480° F. |
| | barrel (forward) | 450° F. |
| | barrel (rear) | 400° F. |
| | column top | 210–222° F. |
| Pack pressure | | 340–400 psig |
| Output | | 1.2 lbs/hr |
| Shear rate | | 65 sec$^{-1}$ |
| Spin draw | | 100:1 |

The spun yarn is then drawn under the following conditions:

| | |
|---|---|
| Stage 1 | |
| Temperature | 220° F. |
| Ratio | 5:1 |
| Stage 2 | |
| Temperature | 280° F. |
| Ratio | 1.2:1 |
| Draw (overall) | 6:1 |

The spun, drawn yarn is then woven into test strips which are exposed to a xenon arc in an Atlas Weather-Ometer until failure occurs. Failure is considered to occur when the strip loses 50% of its original breaking strength.

The results obtained are shown below along with the results obtained with a control yarn which contained the calcium stearate and the antioxidant.

|  | Hours to Failure |
|---|---|
| Example 3 | 1030 |
| Control | 200 |

COMPARISON EXAMPLE

The procedure of Example 3 is followed in every detail except that an oligomer of 2,4-dichloro-6-t-octylamino-1,3,5-triazine and 4,4'-(hexamethylenediimino)bis-(2,2,6,6-tetramethylpiperidine) is substituted for the product of Example 2. This product is the commercial product which has evolved from U.S. Pat. No. 4,086,204, discussed above. The results obtained are shown below:

|  | Hours to Failure |
|---|---|
| Comparison Example | 785 |
| Control | 200 |

Comparison of the results obtained above with those obtained in Example 3 illustrates the significant improvement in light stability imparted by the oligomer of the present invention.

What is claimed is:

1. An oligomer of Formula I $$\left[ H{-}N(Y){-}Z{-}N(Y'){-}\underset{N}{\underset{|}{C}}\underset{\substack{N\\ \|\\ N}}{\underset{|}{\bigcirc}}\underset{N}{\underset{\|}{C}}{-}N\underset{H}{\overset{(CH_2)_n-\overset{O}{\overset{\|}{C}}-W}{|}}\right]_{n'} - X \quad (I)$$

wherein W represents $C_1-C_{20}$ alkoxy, or $$-N\diagup\diagdown \begin{array}{c}R\\R^1\end{array}$$

wherein R and $R^1$, which are the same or different, represent hydrogen or $C_1-C_{18}$ alkyl; n is an integer from 1 to 3; Y and $Y^1$ which are the same or different, represent hydrogen, $C_1-C_{20}$ alkyl, or the radical (II)

(II)

wherein $R^2$ represents hydrogen, $C_1-C_{18}$ alkyl, or benzyl; $R^3$ and $R^4$ independently represent $C_1-C_8$ alkyl, benzyl, or phenethyl, or together with the carbon to which they are attached form a $C_5-C_{10}$ cycloalkyl; $R^5$ represents hydrogen, $C_2-C_3$ hydroxyalkyl, $C_1-C_8$ alkyl, hydroxyl, or oxyl; Z represents $C_2-C_{20}$ alkylene, either straight-chained or branched, wherein the alkylene chain may be interrupted by oxy, thio, or $$-\overset{R^6}{\underset{|}{N}}-$$

radicals, wherein $R^6$ represents hydrogen, $C_1-C_{20}$ alkyl, or the radical (II); $C_5-C_{10}$ cycloalkylene,

[structural formulas shown]

$C_6-C_{12}$ arylene, or $C_8-C_{14}$ aralkylene, n' is an integer greater than 1, and X represents halo, $C_1-C_8$ alkylamino, di($C_1-C_8$)alkylamino, pyrrolidyl, or morpholino, with the proviso that at least one moiety of formula (II) is present in the repeating unit.

2. The oligomer of claim 1 wherein Y and Y' are the radical (II).

3. The oligomer of claim 1 wherein Y and Y' are each 2,2,6,6-tetramethyl-4-piperidyl and Z is hexamethylene.

4. The oligomer of claim 3 wherein W is alkoxy $C_1-C_{20}$.

5. The oligomer of claim 3 wherein W is ethoxy and n is 1.

6. A method for stabilizing a polymer which is normally subject to degradation by ultra-violet radiation which comprises incorporating into said polymer an ultra-violet stabilizingly effective amount of an oligomer of claim 1.

7. The method of claim 6 wherein the oligomer is incorporated in a concentration of from about 0.2 to 2% based on the weight of the polymer to be stabilized.

8. The method of claim 6 wherein the polymer to be stabilized is a polyolefin.

9. The method of claim 8 wherein the polyolefin is polypropylene.

10. The method of claim 9 wherein the polymer is in the form of multifilaments.

11. The method of claim 7 wherein the oligomer is that of claim 2, 3, 4 or 5.

12. The composition produced by the method of claim 7, 8, 9 or 10.

13. The composition produced by the method of claim 11.

* * * * *